US010847051B2

(12) United States Patent
Bennett et al.

(10) Patent No.: US 10,847,051 B2
(45) Date of Patent: *Nov. 24, 2020

(54) GAIT FEEDBACK SYSTEM

(71) Applicant: PACE, LLC, North Hollywood, CA (US)

(72) Inventors: Charles Laurin Bennett, North Hollywood, CA (US); Nicolas Alexandre DiBenedetto, San Francisco, CA (US)

(73) Assignee: PACE, LLC, North Hollywood, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/111,096

(22) Filed: Aug. 23, 2018

(65) Prior Publication Data
US 2019/0066532 A1    Feb. 28, 2019

Related U.S. Application Data

(60) Provisional application No. 62/549,364, filed on Aug. 23, 2017.

(51) Int. Cl.
*A43B 3/00* (2006.01)
*G09B 19/00* (2006.01)
(Continued)

(52) U.S. Cl.
CPC .......... *G09B 19/003* (2013.01); *A43B 3/0015* (2013.01); *A43B 3/0021* (2013.01);
(Continued)

(58) Field of Classification Search
CPC ..... A43B 3/005; A43B 3/0021; A43B 13/183; A43B 21/30; A43B 13/182; A43B 13/18; A43B 13/181; A43B 3/0005
(Continued)

(56) References Cited

U.S. PATENT DOCUMENTS 621,892 A    3/1899  Azzimonti
1,172,613 A *  2/1916  Larsen ................ A43B 13/183
36/37
(Continued)

FOREIGN PATENT DOCUMENTS

DE    19810182 C1    3/2000

OTHER PUBLICATIONS

Sternbergh, You Walk Wrong, New York Magazine, retrieved from the internet on Mar. 7, 2019 from http://hymag.com/health/features/46213/index4.html#print, published Apr. 21, 2008, 10 pgs.
(Continued)

*Primary Examiner* — Marie D Bays
(74) *Attorney, Agent, or Firm* — Anatoly S. Weiser, Esq.; IPLCounsel.com (57) ABSTRACT

A system may be provided for incorporation in an article of footwear that has an upper coupled to a sole, where the sole has an insole and an outsole and the upper and the insole define an interior space for receiving a foot of a user. The system may include a device configured to be coupled to the footwear beneath the user's foot and a structure for fixing the device in place in a predetermined position in the footwear. In such system, the structure may include a compressible portion coupled to a substantially incompressible portion, and the device may be directly supported by the hard plastic portion of the structure to provide a feedback signal to the user when a pressure applied to the device by the user's foot exceeds a threshold value.

17 Claims, 5 Drawing Sheets

(51) Int. Cl.
*A61B 5/103* (2006.01)
*A43B 19/00* (2006.01)
*A43B 5/06* (2006.01)
*A61B 5/00* (2006.01)

(52) U.S. Cl.
CPC ............... *A43B 5/06* (2013.01); *A43B 19/00* (2013.01); *A61B 5/1038* (2013.01); *A61B 5/486* (2013.01); *G09B 19/0038* (2013.01); *A61B 5/7405* (2013.01); *A61B 5/7455* (2013.01); *A61B 2505/09* (2013.01)

(58) Field of Classification Search
USPC .................................. 36/136, 38, 139, 28, 27
See application file for complete search history.

(56) References Cited

U.S. PATENT DOCUMENTS

| | | | |
|---|---|---|---|
| 4,253,254 A | 3/1981 | Gill | |
| 4,638,575 A * | 1/1987 | Illustrato | A43B 21/30 36/28 |
| 4,709,489 A * | 12/1987 | Welter | A43B 21/30 36/27 |
| 4,956,628 A | 9/1990 | Furlong | |
| 5,014,041 A | 5/1991 | Rosen | |
| 5,036,851 A | 8/1991 | Cohen | |
| 5,040,313 A | 8/1991 | Simjian et al. | |
| 5,269,081 A * | 12/1993 | Gray | A43B 7/00 36/136 |
| 5,357,696 A * | 10/1994 | Gray | A43B 7/00 36/136 |
| 5,381,608 A * | 1/1995 | Claveria | A43B 21/30 36/35 R |
| 5,421,107 A | 6/1995 | Bryan | |
| 5,422,628 A | 6/1995 | Rodgers | |
| 5,438,768 A | 8/1995 | Bauerfeind | |
| 5,500,635 A | 3/1996 | Mott | |
| 5,566,479 A * | 10/1996 | Gray | A43B 3/0005 36/1 |
| 5,592,759 A | 1/1997 | Cox | |
| 5,640,788 A | 6/1997 | Thange | |
| 5,647,147 A | 7/1997 | Coomer | |
| 5,765,300 A | 6/1998 | Kianka | |
| 5,883,569 A | 3/1999 | Kolefas | |
| 6,031,463 A * | 2/2000 | Bechmann | A61B 5/1036 340/572.1 |
| 6,082,024 A | 7/2000 | Del Biondi | |
| 6,087,926 A * | 7/2000 | Hajianpour | A43B 3/0005 340/573.1 |
| 6,122,846 A * | 9/2000 | Gray | A43B 3/0005 340/573.1 |
| 6,195,915 B1 | 3/2001 | Russell | |
| 6,237,256 B1 | 5/2001 | Maki et al. | |
| 6,356,856 B1 | 3/2002 | Damen et al. | |
| 6,360,597 B1 | 3/2002 | Hubbard, Jr. | |
| 6,405,606 B1 * | 6/2002 | Walczyk | A43D 1/00 36/136 |
| 6,622,401 B2 | 9/2003 | Carroll, III | |
| 6,732,456 B2 | 5/2004 | Hussain | |
| 7,100,307 B2 | 9/2006 | Burke et al. | |
| 7,124,518 B1 | 10/2006 | Brown | |
| 7,254,910 B2 | 8/2007 | Guzman | |
| 7,272,900 B1 | 9/2007 | Epstein | |
| 7,331,124 B2 * | 2/2008 | Meschan | A43B 13/186 36/27 |
| 7,353,137 B2 | 4/2008 | Vock et al. | |
| 7,360,326 B1 | 4/2008 | Tanaka | |
| 7,426,873 B1 | 9/2008 | Kholwadwala et al. | |
| 7,493,810 B2 * | 2/2009 | Walczyk | G01L 1/04 200/1 B |
| 7,584,556 B2 | 9/2009 | Fujita et al. | |
| 7,596,888 B2 | 10/2009 | Meschan et al. | |
| 7,607,243 B2 * | 10/2009 | Berner, Jr. | A43B 3/0005 36/136 |
| 7,620,520 B2 | 11/2009 | Vock et al. | |
| 7,908,774 B2 | 3/2011 | Mirza et al. | |
| 7,997,007 B2 * | 8/2011 | Sanabria-Hernandez | A43B 3/0005 36/1 |
| 8,166,671 B2 * | 5/2012 | Frederick | A43B 13/183 36/27 |
| 8,167,824 B2 | 5/2012 | Iwata et al. | |
| 8,308,665 B2 | 11/2012 | Harry et al. | |
| 8,458,929 B2 | 6/2013 | Carnes et al. | |
| 8,584,382 B2 * | 11/2013 | Holzer | A43B 3/0005 36/136 |
| 8,676,541 B2 | 3/2014 | Schrock et al. | |
| 8,749,115 B2 | 6/2014 | Pas et al. | |
| 8,950,086 B2 | 2/2015 | Andriacchi et al. | |
| 9,032,647 B2 | 5/2015 | Carnes et al. | |
| 9,055,778 B1 | 6/2015 | Kelley et al. | |
| 9,549,585 B2 | 1/2017 | Amos et al. | |
| 2002/0093428 A1 * | 7/2002 | Bechmann | A61B 5/1038 340/573.1 |
| 2006/0156588 A1 * | 7/2006 | Ferrell | A43B 3/00 36/136 |
| 2006/0230640 A1 * | 10/2006 | Chen | A43B 3/0005 36/136 |
| 2007/0028484 A1 * | 2/2007 | Akhidime | A43B 13/181 36/28 |
| 2007/0101612 A1 * | 5/2007 | Kilgore | A43B 13/20 36/28 |
| 2008/0041169 A1 * | 2/2008 | Walczyk | G01L 1/04 73/862.391 |
| 2008/0066343 A1 * | 3/2008 | Sanabria-Hernandez | A43B 3/0005 36/43 |
| 2008/0287832 A1 * | 11/2008 | Collins | A43B 3/0005 600/587 |
| 2009/0019729 A1 * | 1/2009 | Nakano | A43B 7/14 36/91 |
| 2009/0139114 A1 * | 6/2009 | Malek | A43B 7/144 36/3 B |
| 2009/0229143 A1 * | 9/2009 | Meschan | A43B 13/186 36/88 |
| 2009/0234249 A1 * | 9/2009 | Randolph | A43B 3/0005 600/592 |
| 2012/0159810 A1 * | 6/2012 | Klassen | A43B 13/181 36/28 |
| 2015/0177081 A1 * | 6/2015 | Steier | G01L 1/205 600/592 |
| 2016/0029926 A1 * | 2/2016 | Varnum | A61B 5/1036 73/172 |
| 2017/0027512 A1 * | 2/2017 | Yuan | A61B 5/6829 |
| 2017/0135417 A1 * | 5/2017 | Lucrecio | A61B 5/1038 |
| 2017/0265560 A1 * | 9/2017 | Beers | A43B 3/0005 |
| 2018/0256071 A1 * | 9/2018 | Mathieu | A43B 3/0005 |
| 2018/0263532 A1 * | 9/2018 | Smulyan | A61B 5/112 |

OTHER PUBLICATIONS

Lieberman, The Barefoot Professor: by Nature Video, YouTube, retrieved from the Internet on Mar. 7, 2019 from https://www.youtube.com/watch?v=7jmj-7YKZE&feature=youtu.be, published Jan. 27, 2010, 3 pages.

Hamilton, Study: Orthotics Don't Improve Running Biomecahnics, Runner's World, retrieved from the internet on Mar. 7, 2019 from https://www.runnersworld.com/health-injuries/a20798062/study-orthotics-dont-improve-running-biomechanics/, published Mar. 8, 2013, 6 pages.

Letters to the Editor-In-Chief, Journal of Orthopaedic & Sports Physical Therapy, vol. 42, No. 2, pp. 146-148, retrieved from the internet on Jul. 17, 2017 from https://www.jospt.org/doi/pdf/10.2519/jospt.2012.0201, published Feb. 2012, 3 pages.

Riches, Brake Force at Heel Strike Does the Most Damage in Runners, Run Forefoot, retrieved from the internet on Mar. 7, 2019 from http://runforefoot.com/heel-striking-brakes-running/, published Apr. 8, 2014, 6 pages.

Lieberman et al., Effects of Stride Frequency and Foot Position at Landing on Braking Force, Hip Torque, Impact Peak Force and the (56) References Cited

OTHER PUBLICATIONS

Metabolic Cost of Running in Humans; The Company of Biologists, Journal of Experimental Biology (2015) 218, 3406-3414, published Aug. 26, 2015, 9 pages.
U.S. Receiving Office, International Search Report in International Patent Application No. PCT/US 18147827, dated Dec. 10, 2018, 2 pages.
U.S. Receiving Office, Written Opinion of the International Searching Authority in International Patent Application No. PCT/US 18/47827, dated Dec. 10, 2018, 35 pages.
Lieberman et al., Biomechanics of Foot Strikes & Applications to Running Barefoot or in Minimal Footwear, Harvard University Skeletal Biology Lab, retrieved from the internet on Mar. 7, 2019 from http://www.barefootrunning.fas.harvard.edu/, 2 pages.

* cited by examiner

GAIT FEEDBACK SYSTEM

CROSS-REFERENCE TO RELATED APPLICATION

This application claims the benefit under 35 U.S.C. § 119(e) of the priority of U.S. Provisional Patent Application Ser. No. 62/549,364, filed Aug. 23, 2017, the entirety of which is hereby incorporated by reference for all purposes.

FIELD OF THE DISCLOSURE

The field of the present disclosure includes a system for providing to a wearer of a shoe a sensory feedback indicating characteristics of the gait and stance of the wearer, including the force of heel strike and overstriding. Various configurations of embodiments of the present disclosure may notify the wearer when a force at the wearer's foot exceeds a desired threshold at a specific or general area of the foot. The notification through the sensory feedback may be with regards to an initial foot strike or at any time the foot is bearing some weight during walking, running or standing. The field also includes the system for providing the sensory feedback as an audible sound or as haptic feedback.

BACKGROUND AND SUMMARY OF THE DISCLOSURE

Devices have been proposed for use at a toe-end in a child's shoe to produce a sound to indicate when the child's foot has grown over the device in the toe-end. In particular, U.S. Pat. No. 5,014,041 to Rosen describes a Shoe Fitting System for children's shoes, and shows in FIGS. 8 and 9 a spring 66 at the toe-end of the shoe that begins clicking when the child's foot grows over the spring. FIGS. 10 and 11 of Rosen show electrical pressure switches in the heel 74 (to check that the child's foot is not shifted forward in the shoe) and toe 76 connected to a circuit to make an audible response, again as the child's foot grows over the toe-end switch. The disclosure of Rosen does not provide any teaching relating to the wearer's foot-strike mechanics in a walking or running gait.

A dancer's shoe is disclosed in U.S. Pat. No. 621,892 to Azzimonti, with a bell b1 in heel B for the purpose of entertainment. The shoe has a striker b2 that rings bell b1 only when the dancer stomps his or her foot. Like Rosen, the disclosure in Azzimonti lacks any suggestion for how to provide the wearer with feedback on the wearer's foot-strike mechanics in a walking or running gait. Similarly, U.S. Pat. No. 4,253,254 provides a squeaker in the heel of a shoe, generally designed to make noise on each step, again without feedback on characteristics of the wearer's foot-strike mechanics.

Several patents, such as U.S. Pat. No. 7,997,007, disclose electronic systems, including heel and toe sensors coupled to a computer and/or amplifier that may produce tones indicating a particular foot-strike pattern. However, such a system is complex, expensive, and difficult for a user to operate.

A system according to one or more embodiments of the present disclosure provide a shoe or insole insert with a mechanical structure producing audio and/or haptic feedback on the wearer's foot-strike mechanics and the wearer's stance during certain conditions.

DETAILED DESCRIPTION OF THE DISCLOSURE

Embodiments of the present disclosure are directed to providing feedback to a wearer of a shoe or other footwear, informing the wearer about force exceeding a desired threshold at a specific or general area of the foot. The sensory feedback may be with regards to an initial foot strike or at any time the foot is bearing some weight during walking, running or standing. For example, feedback regarding gait, foot strike pattern, or weight distribution through a ground contact phase. Additional examples include feedback about whether the wearer is flat footed while standing.

Some embodiments of the present disclosure provide the feedback to the wearer about his or her gait while running or walking. The device may provide a measure, at least as a single-point indicator of exceeding a threshold of a force vector, i.e., a force and an angle at impact, and/or force and angle during ground contact as weight is transferred forward on the foot.

Figure 1:
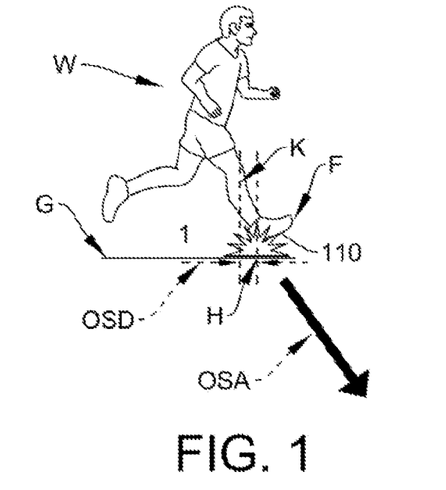
FIG. 1 is a pictorial side view of a person running with overstriding.
Figure 2:
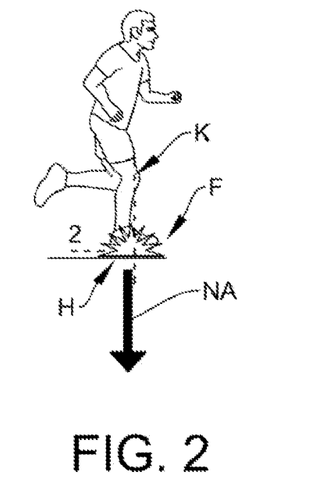
FIG. 2 is a pictorial side view of a person running without overstriding.

One example of such feedback is to provide a signal when the wearer overstrides, i.e., when, during running or walking, a foot is lifted and moved forward and, on impact with the ground, lands in front of the knee with the tibia not vertical. Conversely, the absence of feedback from the device informs the wearer of a non-overstriding condition, providing negative reinforcement to the wearer of the preferred gait or weight distribution. In negative reinforcement, a desired response or behavior is strengthened by stopping, removing or avoiding a negative outcome or aversive stimulus. FIGS. 1 and 2 illustrate this in a running gait, in both cases at the point where foot F is just being brought back into contact with the ground G after being lifted and moved forward. Additionally, embodiments of the present disclosure may be configured to provide positive reinforcement to the wearer, for example, by providing a feedback signal to the wearer while running or walking with the desired gait or in a desired stance.

FIG. 1 illustrates a running gait where person W overstrides with a heel strike. The location where foot F hits ground G is forward of knee K by an overstride distance OSD. In this particular illustrated circumstance, the person's heel H is the first portion of foot F to strike the ground with the sole of the foot not horizontal to ground G. The angle of the tibia in the overstriding condition is shown by arrow OSA, which is not near vertical. In this case of overstriding with heel strike, the force of the strike at the heel is significant and is associated with a braking force that tends to decelerate the person's body. Other circumstances and foot strike patterns may also involve overstriding, and the angle of the tibia (lower leg) at impact is understood to be a determinant of overstriding. That is, the tibia being near vertical at ground impact indicates a stride length that typically is preferred, although this varies for different running styles. Generally, a heel strike is frequently an aspect of overstriding, although it is possible to overstride with a midfoot or forefoot strike pattern. Embodiments of the present disclosure may be used as a tool to train the wearer towards the practice of a gait that is preferred for a particular running style.

FIG. 2 illustrates, at the point of ground-contact of the forward foot, a running gait without overstriding. Here the person's foot F strikes the ground with heel H behind knee K and the tibia is near vertical. The example of a non-overstriding condition illustrated in FIG. 2 includes that foot F strikes the ground in a flat orientation, i.e., with the sole parallel to the ground also known as a midfoot strike, with the weight distributed roughly evenly between the heel and forefoot. Alternatively, in the non-overstriding condition the forefoot might strike before the heel (known as a forefoot strike), or the heel might strike slightly before the forefoot. In some instances of a non-overstriding condition the foot is striking the ground roughly parallel to the ground, although this varies runner to runner. In the non-overstriding condition the braking force of strike at the heel is typically small or insignificant relative to the overall impact of the foot, and the downward force at the heel is less than or equal to the downward force at the forefoot.

Overstriding is understood to impose suboptimal energy costs on a runner, and a runner wanting to stop overstriding may be assisted by a system that informs the runner as overstriding is occurring. Similarly, informing a person of a detrimental foot strike pattern as the pattern is occurring may be useful for correcting such patterns or undesirable weight distribution during ground contact.

Figure 3:
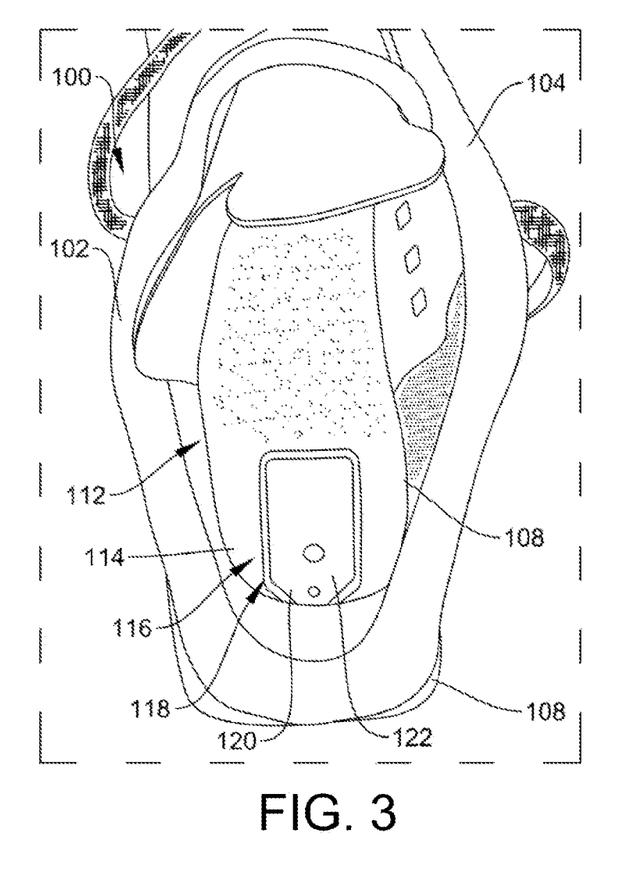
FIG. 3 is an overhead view of a feedback device in accordance with an embodiment of the present disclosure in a shoe with an insole insert.

As shown in FIG. 3, a system 100 in accordance with one or more embodiments of the present disclosure may include a shoe 102 that includes an upper 104 coupled to a sole 106. Sole 106 includes an insole 108 and an outsole 110 (FIG. 1). Inside shoe 102, upper 104 and insole 108 define an interior space 112 for receiving a foot F of a user W (see FIGS. 1 and 2). Insole 108 may include an insert 114, typically made of a soft foam, such as EVA.

A feedback device 116 may be positioned in shoe 102 between the wearer's foot and sole 106 of the shoe, for example below the heel of the wearer's foot, and preferably the rear portion of the heel area, as shown in FIG. 3. Insert 114 may include a cutout area 118 to receive and fix in location the feedback device. Feedback device 116 may include a base 120 supporting a spring 122 configured to provide audio and haptic feedback to the wearer under certain conditions, such as overstriding.

Figure 4:
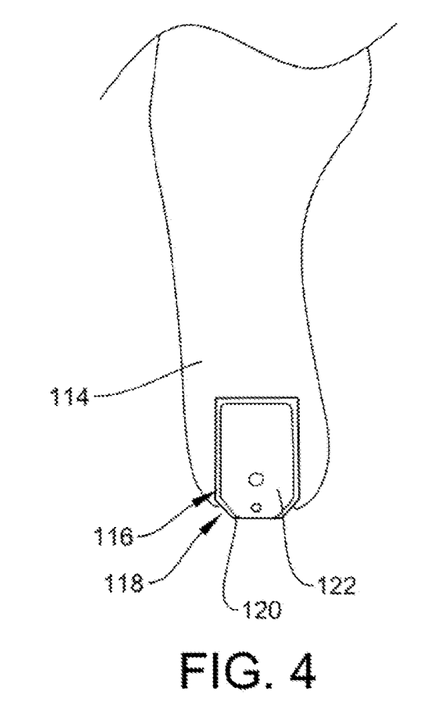
FIG. 4 is a perspective view of the feedback device of FIG. 3 with the insole insert out of the shoe.

FIG. 4 shows feedback device 116 still within insert 114 but with both removed from the shoe. Feedback device 116, base 120, spring 122, and/or insert 114 may be built into the shoe or one or more of these may be removable, as illustrated by FIG. 4.

Cutout area 118 may be shaped to receive base 120, which in turn may support spring 122. Insert 114 and base 120 may provide a structure for fixing spring 122 in place in a predetermined position in the shoe, e.g., in the heel area of the shoe where it can provide feedback to the wearer on whether or not the wearer is overstriding. Insert 114 is typically is made of a compressible material, such as EVA foam or similar material generally selected for the wearer's comfort. Base 120 is typically made of a substantially incompressible material, such as a hard plastic, e.g., ABS, which may provide a direct, substantially fixed support to spring 122, allowing spring 122 to respond with feedback to the pressure that the wearer's heel exerts on the spring and the base.

Figure 5:
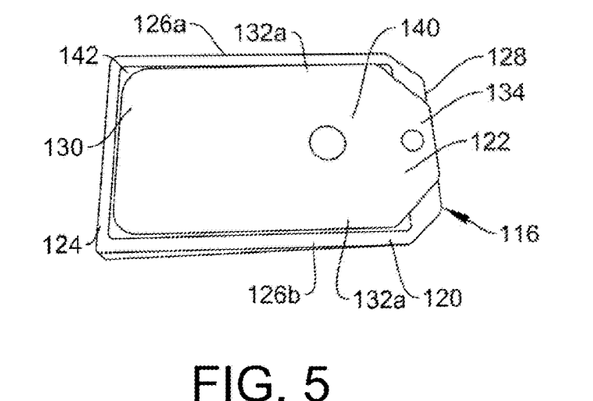
FIG. 5 is a perspective view of the spring and the base of the feedback device, with the spring in place.

Base 120 and spring 122 are shown separate from the insert in FIG. 5. Base 120 may be substantially rectangular and include forward edge 124, side edges 126a and 126b, and rear edge 128. Spring 122 may be deployed on base 120 with the spring's forward edge 130 and side edges 132a and 132b fitted between the corresponding edges of base 122. A rear edge 134 of spring 122 may rest on edge 128 of base 120.

Typically spring 122 is a substantially flat piece of metal, e.g., steel, that may be formed by stamping. Spring 122 may include an upwardly dimpled portion 140 that can deform abruptly downwardly under a specified pressure or force, and, in doing so, provide an audible sound, such as a click sound, and a haptic feedback indicating the deformation. The abrupt deformation is typically a characteristic of the dimpled steel, although it may be formed for a more gradual deformation, or formed with different structure, and detect the pressure or force and provide feedback within the scope of the present disclosure.

Figure 4A:
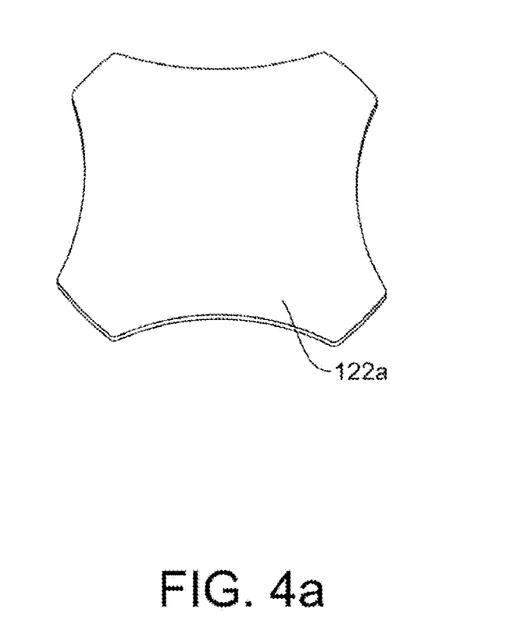
FIG. 4a is a perspective view of an example spring of the feedback device, with the spring in place.

Spring 122 may, for example, be a tactile dome spring and may be designed to meet one or more performance criteria. These criteria may include a specific actuation force, the physical dimensions of the spring, and the quality of the sound produced by the spring at actuation. For example, the spring actuation force, expressed as a weight may be about 8.8 pounds or 4,000 grams and the spring may have a height of 1.5-mm and width of 25-mm. The spring may be tuned to produce a sound at actuation or alternatively may be tuned to be substantially silent. In either case, the spring may offer haptic feedback to the wearer at actuation. An example of a dome spring 122a is shown in FIG. 4a. Such a dome spring may be obtained, e.g., from Snaptron: see https://www.snaptron.com/part-number/gx252000/.

As an example of operation in use, if the wearer is running with an overstride that includes a heel strike pattern, the wearer's heel on each foot strike will apply pressure at dimpled portion 140 of spring 122, causing deformation at dimpled portion 140, producing an audible click sound and a haptic feedback of the dimpled portion dropping relative to the rest of the spring and moving downwardly away from the wearer's heel. As the spring deforms away from the wearer's heel the user may feel this as a sudden drop underneath that part of their foot. A typical overstride involves the wearer's heel striking first, although this is not always the case, but the overstriding is expected to provide pressure to spring 122. The strength of the material and dimensions of spring 122 and its dimpled portion 140, as well as the supporting geometry and the hardness of base 120, may be selected for detecting when the pressure applied to the device by the user's foot exceeds a threshold value that is characteristic of an undesired gait. For example, the threshold value may be selected to detect heel striking.

As shown in FIG. 5, spring 122 rests on base 120 and may be held in place by any suitable means. For example, adhesive tape 142 provides a hinged connection of spring 122 to base 120.

Figure 6:
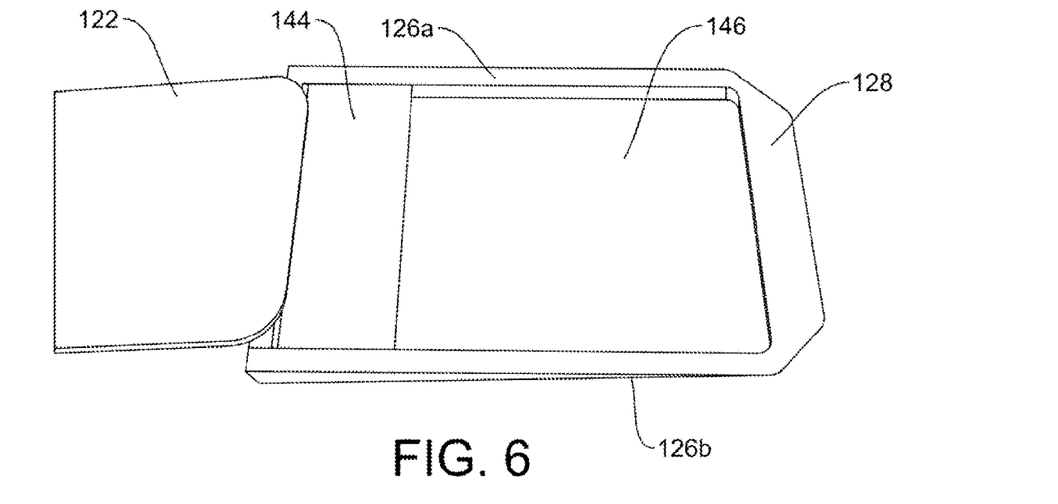
FIG. 6 is a perspective view of the spring and the base of the feedback device, with the spring flipped out of the way to show more of the base.

The supporting geometry of base 120 is shown in FIG. 6, where spring 122 has been flipped over forward edge 124. Adjacent forward edge 124, base 122 provides a ridge 144 for supporting spring 122 at edge 130 in conjunction with the support by base edge 128 of spring rear edge 134. A recessed portion 146 of base 120 extending between base edges 124 and 128 may facilitate spring 122 flexing and deforming at dimpled portion 140 under pressure from the wearer's foot.

With reference to FIGS. 5 and 6, either or both of spring 122 and base 120 may be varied to adjust the threshold at which the spring deforms. For example, the diameter of the dimpled portion may be varied and/or the base's span between its edges that support the spring may be varied. Each of these affect the force at which the spring deforms, in addition to other characteristics as described above.

Figure 5A:
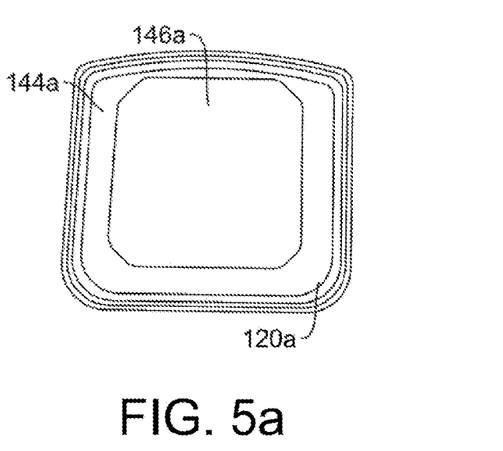
FIG. 5a is a perspective view of another example of a base for the feedback device, without the spring in place.
Figure 6A:
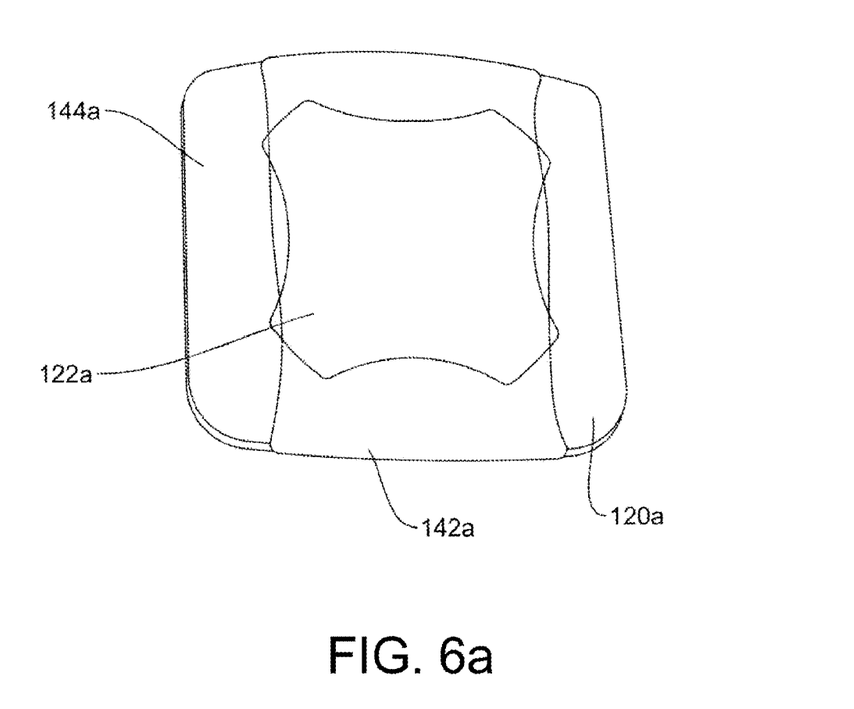
FIG. 6a is a perspective view of the spring of FIG. 4a and the base of FIG. 5a for the feedback device, with the spring in place.

A base 120a is shown in FIG. 5a having an alternative construction that nay be used, e.g., with dome spring 122a of FIG. 4a. Dome spring 122a may be operational fir actuation in base 120a on a substantially flat surface 146a in base 120a. The supporting geometry of base 120a is similar to base 120. Base 120a provides a ridge 144a that may substantially surround flat surface 146a and the ridge may provide four corners for supporting each of the four corners of spring 122a, as best seen in FIG. 6a. Spring 122a may be held in place in base 120a by any suitable means, such as shrink-wrap material 142a. Thus, base 120a may facilitate spring 122a flexing and deforming under pressure from the wearer's foot similar to the operation of the base 120 and spring 122a.

The foregoing embodiment of the present disclosure is an example of how a feedback device provides information to the wearer about the wearer's foot strike pattern. This particular example is directed toward detection of a heel strike pattern, which may be useful for the wearer's eliminating, reducing, or changing that foot strike pattern and/or an overstriding gait. Variations on the structure may provide additional information about the wearer's foot strike pattern and gait. Embodiments of the present disclosure encompass the providing of a wide variety of information about the strike pattern and gait. Feedback devices in accordance with the present disclosure may be arranged to detect and inform the wearer about the angle of the foot relative to the ground at impact in either or both of the sagitall plane and the coronal plane. That is, feedback devices may be used in detecting heel, midfoot, and forefoot strikes, as well as striking on the inside or outside of the foot, and/or characteristics of the foot's pronating and/or supinating during the period of contact with the ground. The feedback devices may detect the undesired weight distribution during impact and/or during the period of ground contact as a function of the wearer's pace. For example, the threshold value may be set so that a low impact heel strike at walking pace does not trigger the feedback device, while a heel strike at a faster pace will trigger the feedback device.

Figure 7:
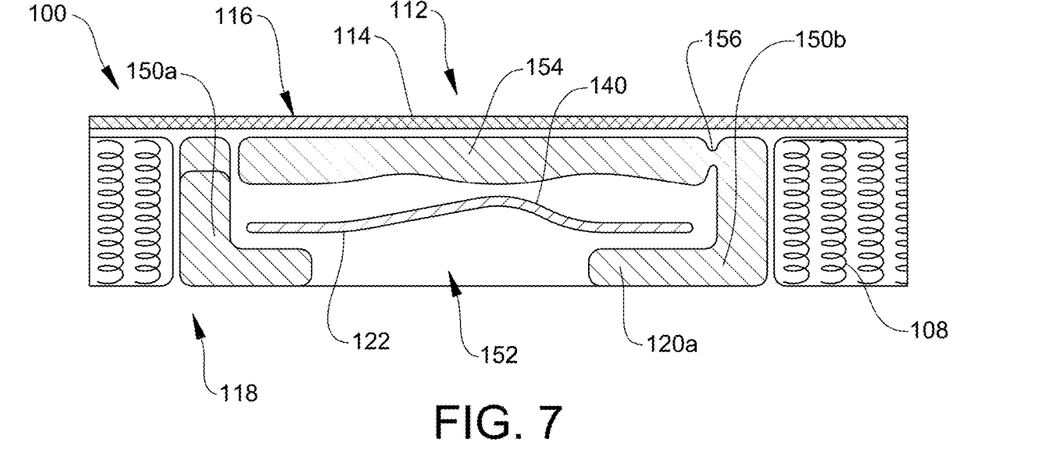
FIG. 7 is a cross-sectional view of the feedback device with an alternatively configured base.

FIG. 7 is a cross-sectional view of the feedback device with an alternatively configured base 120a for spring 122. Base 120a includes side edges 150a and 150b with a recessed or cutout portion 152 therebetween providing support for spring 122 while facilitating deformation at dimpled portion 140. Base 120a may also include a trigger 154 with a hinge 156, which may be integrally formed with the rest of base 120a, coupling trigger 154 to one of edges 150a or 150b. Materials, geometry, and operation of base 120a may be otherwise substantially similar to base 120, while trigger 154 and hinge 156 may provide additional selectable variations for setting the threshold value for device 116 to provide feedback to the wearer.

Figure 8A:
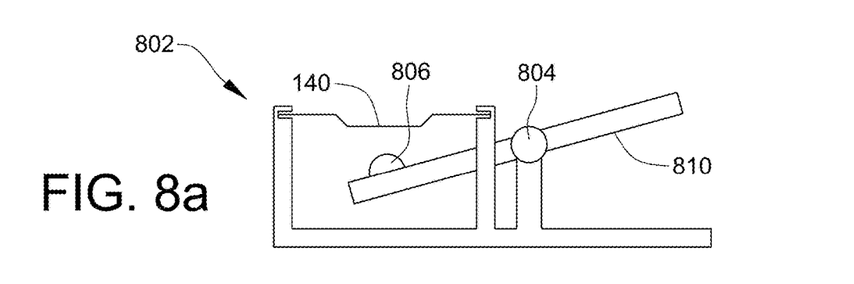
FIG. 8a is a side cross-sectional view of a layout of a seesaw configuration for an embodiment of the present disclosure with the lever arm not depressed.
Figure 8B:
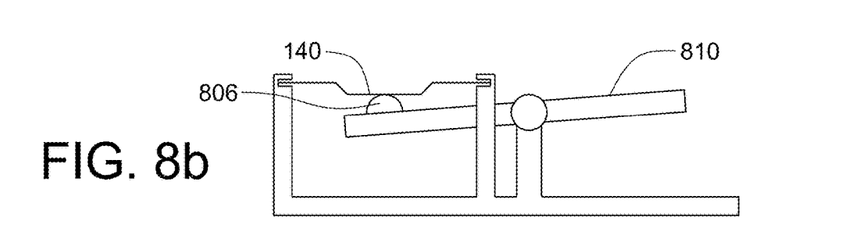
FIG. 8b is a side cross-sectional view of a layout of a seesaw configuration for an embodiment of the present disclosure with the lever arm partially depressed to the point it is about to trigger the spring.
Figure 8C:
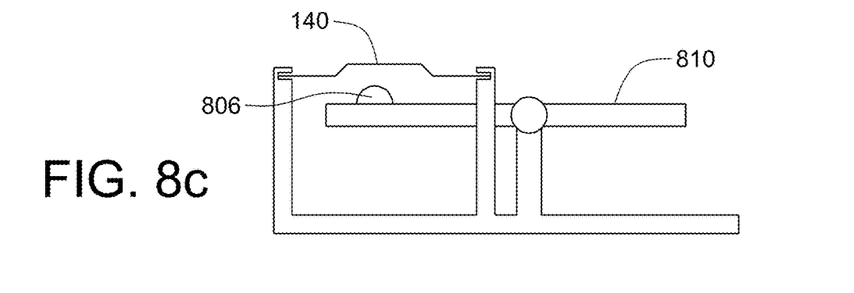
FIG. 8c is a side cross-sectional view of a layout of a seesaw configuration for an embodiment of the present disclosure with the lever arm depressed to the extent it has pushed the pressure point sufficiently to trigger the spring, inverting the dimpled portion and providing feedback to the wearer.

The foregoing embodiments generally provide the feedback device with a button on a spring where a force directed roughly perpendicularly to a raised section of the spring causes the spring to deform, and alternative transformations of the force may be provided for particular applications in embodiments of the present disclosure. For example, as shown in FIGS. 8a-c, a lever configuration 802 may include a fulcrum 804 and a pressure point 806 on a lever arm 808 that applies the force to the raised section 140 of the spring 122 during an undesired foot strike pattern. As shown in the progression of FIGS. 8a, 8b, and 8c, the lever arm 810 is not depressed in 8a; the lever arm is partially depressed in 8b to the point it is about to trigger the spring; and in 8c the lever arm's depression has pushed the pressure point sufficiently to trigger the spring and invert dimpled portion 140, providing feedback to the wearer. In this embodiment the direction of the force may be reversed and/or more or less force may be required to deform spring depending on the position of the fulcrum nearer or further out on lever arm, as best suited for a particular application. In such configuration, the fulcrum and/or pressure point may be moved to adjust the threshold value for spring deformation. In the embodiment depicted in FIGS. 8a-c the seesaw lever provides the fulcrum in the middle and the dimpled portion of the spring protrudes downward and is positioned above the unloaded lever arm, while other embodiments may of such seesaw lever may receive a force from below and transfer that force to an upwardly facing dimpled portion.

Figure 9A:
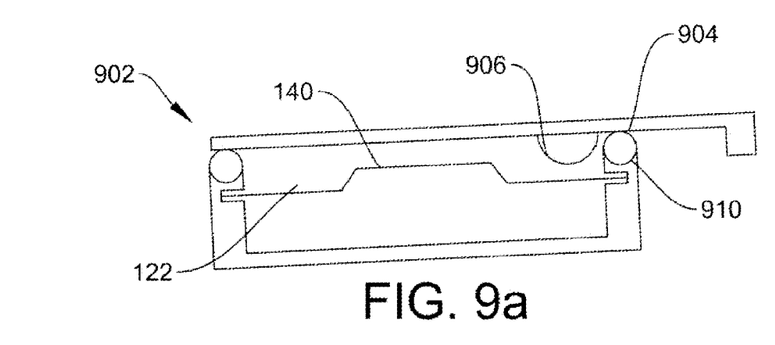
FIG. 9a is a side cross-sectional view of a layout of a slider configuration for an embodiment of the present disclosure with the slider in the non-actuated position.
Figure 9B:
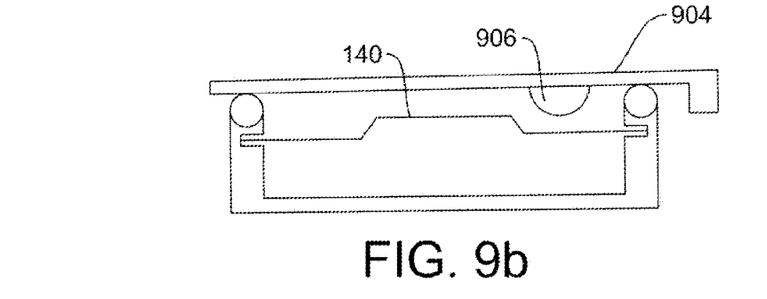
FIG. 9b is a side cross-sectional view of a layout of a slider configuration for an embodiment of the present disclosure with the slider moved toward the actuated position.
Figure 9C:
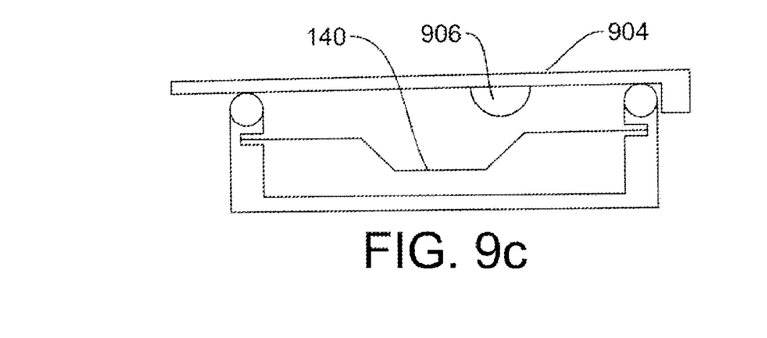
FIG. 9c is a side cross-sectional view of a layout of a slider configuration for an embodiment of the present disclosure with the slider in the actuated position and the spring inverted.

In another alternative embodiment, depicted in FIGS. 9a-c, a slider configuration 902 may include a sliding track 904 on rollers 910 or other bearing surface may be arranged over the raised section 140 of the spring 122, typically to slide parallel to the spring surface. The track and spring are shown in a nominal position in 9a; and partially slid in 9b, almost to the point of triggering the spring; and in the triggered position in 9c, providing feedback to the wearer. In such configuration, overstriding may cause the sliding track to move forward, in turn causing the spring to deform. The embodiment may be particularly useful in detecting the runner's braking force in an undesired gait, such as an overstriding condition.

Figure 10A:
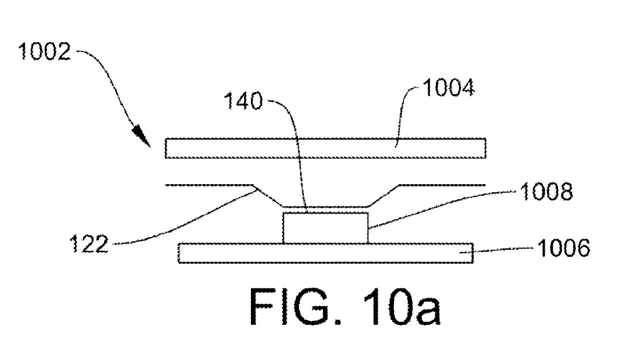
FIG. 10a is a side cross-sectional views of a layout of an inverter configuration for an embodiment of the present disclosure with the actuator not depressed.
Figure 10B:
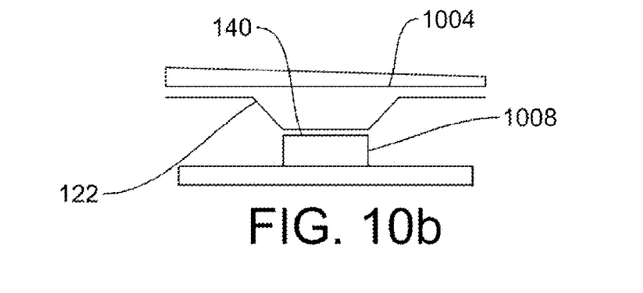
FIG. 10b is a side cross-sectional views of a layout of an inverter configuration for an embodiment of the present disclosure with the actuator partially depressed.
Figure 10C:
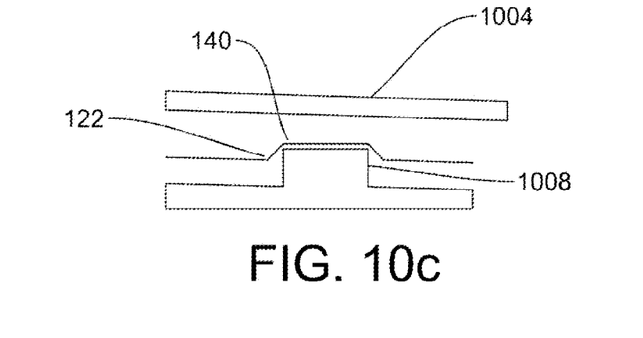
FIG. 10c is a side cross-sectional views of a layout of an inverter configuration for an embodiment of the present disclosure with the actuator sufficiently depressed to invert the spring.

Another embodiment is shown in FIGS. 10*a-c*, where an inverter mechanism 1002 provides for a downward force on spring 122 to trigger a downwardly-facing dimpled portion 140 in an upward direction. Typically with inverter 1002, the wearer's foot is positioned over a bar 1004 overlaying spring 122 and inverter 1002 also has a base 1006 including a raised portion 1008 beneath spring 122 with raised portion 1008 abutting dimpled portion 140 of spring 122. Alternatively, the wearer's foot, sock, and/or a layer of foam, fabric, or similar shoe material may directly overlay spring 122 without bar 1004. In a nominal position as shown in FIG. 10*a*, the wearer's foot and/or bar 1004 are above spring 122, which is in the non-triggered condition. A force downwardly on bar 1004 presses on spring 122, as shown in FIG. 10*b*, pressing dimpled portion 140 against raised portion 1008. As shown in FIG. 10*c*, a sufficient downward force on bar 1004 (and/or an upward force or resistance at raised portion 1008) causes spring 122 to trigger, providing feedback to the wearer.

Embodiments of the present disclosure encompass devices for detecting when pressure exceeds a threshold value in any portion of the shoe sole. The detection may provide sensory feedback when exceeding the threshold value indicates a proper gait as well as an improper gait, depending on the particularly application. For example, a feedback device may be located for the detection of overpronation, underpronation, and/or proper pronation of the wearer's foot, and the feedback device may be configured to provide the sensory feedback on any of the conditions. Other forms of sensory feedback may be used, such as a vibratory haptic feedback.

The feedback device of the present disclosure may be inserted into any footwear or be built into any footwear. This includes any shoe, boot, sandal, sock, or any insert for any of these, including anything that can be positioned beneath the foot.

The feedback device of the present disclosure may be incorporated into instructional and rehabilitation protocols of podiatrists/physical therapists/coaches and may be used to educate/guide patients and athletes toward proper mechanics.

It is believed that the disclosure set forth herein encompasses multiple distinct inventions with independent utility. While each of these inventions has been disclosed in its preferred form, the specific embodiments thereof as disclosed and illustrated herein are not to be considered in a limiting sense as numerous variations are possible. Each example defines an embodiment disclosed in the foregoing disclosure, but any one example does not necessarily encompass all features or combinations that may be claimed. Where the description recites "a" or "a first" element or the equivalent thereof, such description includes one or more such elements, neither requiring nor excluding two or more such elements. Further, ordinal indicators, such as first, second or third, for identified elements are used to distinguish between the elements, and do not indicate a required or limited number of such elements, and do not indicate a particular position or order of such elements unless otherwise specifically stated.

The invention claimed is:

1. A system for incorporation in an article of footwear, the article including a sole and an upper coupled to the sole, the sole comprising an outsole configured to contact a ground surface and an inner sole surface, the upper of the article of footwear and the inner sole surface defining an interior space for receiving a foot of a user, wherein the insert comprises:
   a compressible insert shaped as an insole to be inserted into the interior space and conform substantially to the inner sole surface between the inner sole surface and the bottom of the foot when the foot is in the interior space; and
   a feedback device placed into and attached to the compressible insert, the feedback device including a dome spring, the dome spring comprising a dimpled portion and a substantially flat spring portion, and a substantially incompressible base directly supporting the dome spring at the substantially flat spring portion;
   wherein:
   the dimpled portion of the dome spring faces the bottom of the foot when the user wears the article of footwear and the foot is in the interior space;
   the substantially incompressible base is between the inner sole surface and the substantially flat spring portion of the dome spring when the insert is inserted into the article of footwear and conforms substantially to the inner sole surface;
   the dimpled portion of the dome spring is exposed to the interior space or separated from the interior space by a layer of a compressible material, so that the foot of the user pushes down and releases the dimpled portion when the insert is inserted into the article of footwear so that the compressible insert conforms substantially to the inner sole surface and the user walks or runs wearing the article of footwear; and
   the dome spring is configured to produce a feedback signal to the user when a pressure applied to the dimpled portion of the spring by the foot of the user exceeds a threshold value.

2. The system of claim 1, wherein the feedback signal is an audible sound produced by the dome spring when the dome spring is deformed by the pressure that exceeds the threshold value.

3. The system of claim 1, wherein the feedback signal is a haptic signal produced by the dome spring when the dome spring is deformed by the pressure that exceeds the threshold value.

4. The system of claim 1, wherein the compressible insert comprises a heel area and the feedback device is placed and attached in the heel area.

5. The system of claim 1, wherein the feedback device further comprises a piece of adhesive tape placed to provide a hinged attachment of the dome spring to the substantially incompressible base.

6. The system of claim 5, wherein the substantially incompressible base is made of hard plastic material.

7. The system of claim 1, wherein the feedback device further comprises a piece of shrink-wrap material covering the dimpled portion of the dome spring and attaching the dome spring to the substantially incompressible base.

8. The system of claim 1, wherein the dome spring is configured to produce both an audible sound and a haptic signal when the dome spring is deformed by the pressure that exceeds the threshold value.

9. The system of claim 1, wherein the dome spring has a nominal configuration in the absence of compression pressure exceeding, the threshold value and a deformed configuration in the presence of compression pressure exceeding the threshold value, and the dome spring produces the feedback signal in transitioning between the nominal and deformed configurations.

10. An apparatus comprising the insert of claim 1 and the article of footwear, wherein the insert is placed in the interior space.

11. The system of claim 6, wherein the substantially incompressible base comprises a flat surface and a ridge configured to support the dome spring on the flat surface at an edge of the substantially incompressible base.

12. The system of claim 11, wherein the hard plastic, is ABS material.

13. The system of claim 1, wherein the compressible insert comprises portions defining a cutout area for receiving the feedback device.

14. The system of claim 1, wherein the dome spring is made of dimpled steel.

15. The system of claim 1, wherein the dome spring is about 1.5 mm in height and about 25 mm in width.

16. The system of claim 15, wherein the actuation force of the dome spring is equivalent to the weight of about 4,000 grams.

17. A method of making a shoe insole insert, the method comprising:

providing a compressible insert shaped to be inserted into interior space of the shoe and conform substantially to the inner sole surface of the shoe between the inner sole surface and the bottom of a foot of the wearer of the shoe, the compressible insert including parts defining a cutout at the heel area;

providing, a feedback device that comprises a dome spring having a dimpled top and a spring bottom, the spring bottom being attached to a hard plastic base; and attaching the feedback device to the compressible insert at the heel area of the compressible insert so that the dimpled top faces up and can be compressed by the foot of the wearer of the shoe either directly or directly through a layer of a soft material, the soft material being fabric or foam and being located over the feedback device.

* * * * *